United States Patent
Nandi et al.

(10) Patent No.: US 10,138,197 B2
(45) Date of Patent: Nov. 27, 2018

(54) DIRECT CATALYTIC PARTIAL OXIDATION OF ALLYL ETHER

(71) Applicant: ExxonMobil Research and Engineering Company, Annandale, NJ (US)

(72) Inventors: Partha Nandi, Annandale, NJ (US); Steven L. Suib, Storrs, CT (US); Timothy D. Shaffer, Plainfield, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/904,581

(22) Filed: Feb. 26, 2018

(65) Prior Publication Data

US 2018/0258023 A1    Sep. 13, 2018

Related U.S. Application Data

(60) Provisional application No. 62/470,505, filed on Mar. 13, 2017.

(51) Int. Cl.
*C07C 51/285* (2006.01)
*C07C 51/25* (2006.01)
*B01J 23/34* (2006.01)

(52) U.S. Cl.
CPC ............ *C07C 51/285* (2013.01); *B01J 23/34* (2013.01); *C07C 51/25* (2013.01)

(58) Field of Classification Search
CPC ..... C07C 67/39; C07C 69/533; C07C 51/285; C07C 51/25; B01J 23/34
See application file for complete search history.

(56) References Cited

U.S. PATENT DOCUMENTS 4,792,620 A * 12/1988 Paulik ................. B01J 31/0231
560/232

FOREIGN PATENT DOCUMENTS

JP    6336459 A    12/1994

OTHER PUBLICATIONS

Norskov et al, Nature Chemistry, Towards the Computational Design of Solid Catalysts, 2009, 1, pp. 37-46. (Year: 2009).*
Dapurkar et al, Applied Catalysis A: General, Solvent-free Allylic Oxidation of Cycloolefins over Mesoporous CrMCM-41 Molecular Sieve Catalyst at 1 Atm Dioxygen, 2008, 346, pp. 112-116. (Year: 2008).*
Stepovik et al., "Oxidation of Unsaturated Ethers with the System Aluminum Tri-tert-butylate-tert-Butyl Hydroperoxide", Russian Journal of General Chemistry, 2001, pp. 1802-1806, vol. 71(11), translated from Zhurnal Obshchei Khimii, 2001, pp. 1905-1910, vol. 71(11), MAIK Nauka/Interperiodica Publishing.

* cited by examiner

*Primary Examiner* — Paul A Zucker
(74) *Attorney, Agent, or Firm* — Kristina Okafor; Robert A. Migliorini

(57) ABSTRACT

This disclosure describes a new route to acrylate esters via direct catalytic partial oxidation of allyl ether using heterogeneous manganese oxide catalysts. The method involves forming allyl acrylate by contacting allyl ether, where the allyl ether is in solution with a solvent, with one or more oxidants in the presence of a mesoporous manganese oxide (MnOx) catalyst. Oxygen or peroxide can be used as the oxidant. The yield of and selectivity for acrylate ester can be very high, and process efficiency is improved over current processes.

15 Claims, No Drawings

DIRECT CATALYTIC PARTIAL OXIDATION OF ALLYL ETHER

CROSS-REFERENCE TO RELATED APPLICATIONS

This application claims the benefit of U.S. Provisional Application No. 62/470,505 filed on Mar. 13, 2017, the entire contents of which are incorporated herein by reference.

FIELD

This invention describes a novel heterogeneous catalytic partial oxidation of allyl ether where $O_2$ or peroxide can be used as oxidant. The yield of and selectivity for acrylate ester can be very high.

BACKGROUND

Direct catalytic partial oxidation of allyl ether to acrylate ester is not known. The product, allyl acrylate, is a useful building block—for chemicals and polymers. Acrylate esters can be used as monomers or comonomers in radical or cationic polymerization systems wherein the olefin functionality is retained in the product and can be further modified in subsequent reactions, for example crosslinking, silylation, etc. Furthermore, monomers of this class are useful in light curable coatings, inks and adhesives.

Currently, allyl acrylate can be produced by esterification of acrylic acid and allyl alcohol. Acrylic acid is produced from acrylonitrile, which comes from partial oxidation of propane. Other approaches include the Pd-catlyzed oxidation of propylene in the presence of acrylic acid and the transesterification with alkyl esters of acrylic acid with allyl alcohol.

It would be advantageous to develop a new route to acrylate esters via direct catalytic partial oxidation of allyl ether, which would reduce the number of process steps and improve process efficiency.

SUMMARY

Presented herein is a process for forming allyl acrylate, comprising contacting allyl ether in solution with a solvent with one or more oxidants in the presence of a mesoporous manganese oxide (MnOx) catalyst.

In one form, the oxidant is an oxygen-containing gas, such as air.

In another form, the oxidant is a peroxide.

In yet another form, the oxidant is a mixture of air and a peroxide.

Advantageously, the solvent is selected from acetonitrile, chloroform, dichloromethane, N,N-dimethylformamide, N,N-dimethyl acetamide, dimethyl sulfoxide, or dimethylcarbonate.

In another form, the solution further comprises trichloromethyl cyanide and/or N-hydroxyphthalimide (NHPI).

Conveniently, the mesoporous manganese oxide catalyst is promoted with promoter cations of Group I or Group II metals, such as wherein the promoter ions are selected from the group consisting of Li, Na, K, Rb, Cs, Ca, Sr and Ba and combinations thereof, and are advantageously Li ions.

In another form, the mole ratio of solvent to allyl ether is from about 47:1 to about 200:1, or from about 94:1 to about 190:1.

Advantageously, the conversion of allyl ether to allyl acrylate is from about 10% to about 92%, and the selectivity for allyl acrylate is from about 40% to about 100%.

In another form, the process is conducted at temperatures from about 10° C. to about 110° C., or from about 40° C. to about 90° C., or even from about 45° C. to about 80° C.

In another form, the process is conducted at pressures from about 0.1 atm to about 3 atm.

In another form, the process is conducted over a period of from about 0.1 hour to about 16 hours, or from about 1 hour to about 10 hours, or even from about 2 hours to about 5 hours.

DETAILED DESCRIPTION

Direct catalytic oxidation of allyl ether to acrylate ester is challenging due to the possibility of over oxidizing the product. Typically acrylates are made via ammoxidation of propene. While this route is robust, it can not produce acrylate ester derivatives as they have to be prepared via additional steps. Therefore having a direct catalytic aerobic oxidation route to produce acrylate esters is useful.

The present disclosure describes aerobic partial oxidation of allyl ether using heterogeneous manganese oxide catalysts.

Definitions

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

A/an: The articles "a" and "an" as used herein mean one or more when applied to any feature in embodiments and implementations of the present invention described in the specification and claims. The use of "a" and "an" does not limit the meaning to a single feature unless such a limit is specifically stated. The term "a" or "an" entity refers to one or more of that entity. As such, the terms "a" (or "an"), "one or more" and "at least one" can be used interchangeably herein.

About: As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data. All numerical values within the specification and the claims herein are modified by "about" or "approximately" the indicated value, and take into account experimental error and variations that would be expected by a person having ordinary skill in the art.

And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements). As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

Comprising: In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Any device or method or system described herein can be comprised of, can consist of, or can consist essentially of any one or more of the described elements.

Ranges: Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, etc. and sub-ranges such as 10 to 50, 20 to 100, etc. Similarly, it should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds). In the figures, like numerals denote like, or similar, structures and/or features; and each of the illustrated structures and/or features may not be discussed in detail herein with reference to the figures. Similarly, each structure and/or feature may not be explicitly labeled in the figures; and any structure and/or feature that is discussed herein with reference to the figures may be utilized with any other structure and/or feature without departing from the scope of the present disclosure.

The general reaction pathway of the presently disclosed process is as follows:

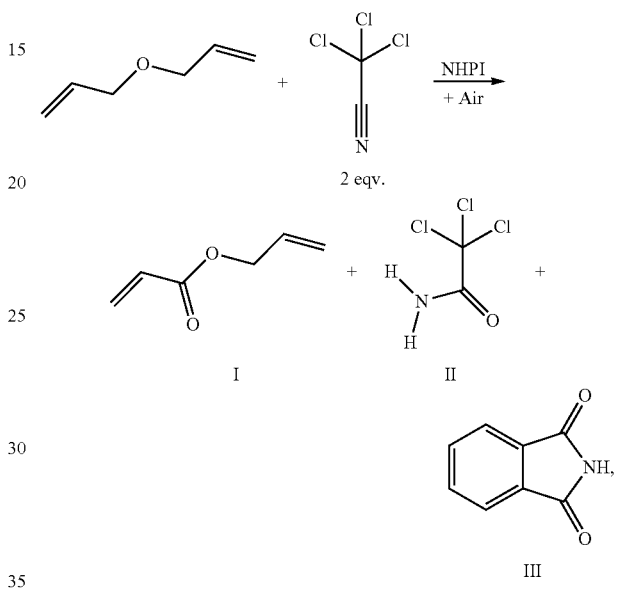

wherein NHPI is N-hydroxyphthalimide and Cl₃CCN is trichloromethyl cyanide. The starting substrate is allyl ether and product I is allyl acrylate. Products II and III are the remanents of trichloromethyl cyanide and NHPI, respectively. Some of the advantages of the disclosed process include (1) allyl acrylate derivatives can be made in a single step, (2) the process uses air and/or peroxides as the oxidizer, and (3) the process uses a heterogeneous catalyst which simplifies separation of the product from the catalyst.

The process can be conducted at relatively low temperatures, such as from about 10° C. to about 110° C., or from about 40° C. to about 90° C., or even from about 45° C. to about 80° C., and at relatively low pressures, such as from about 0.1 atm to about 3 atm. The process can be conducted over a period of from about 0.1 hour to about 16 hours, or from about 1 hour to about 10 hours, or even from about 2 hours to about 5 hours.

Suitable catalysts include mesoporous manganese oxide, either alone or promoted with ions from Groups I or II of the periodic table. For example, the promoter ions can be one or more of Li, Na, K, Rb, Cs, Ca, Sr and Ba and combinations thereof.

Suitable oxidants can be any of a number of peroxides, such as t-butyl hydroperoxide, m-chloroperoxybenzoic acid, cumene hydroperoxide, benzoyl peroxide or peracetic acid. Hydrogen peroxide can be used, but is not as selective as these other peroxides for forming allyl acrylate.

Additionally, oxygen-containing gases, such as air, can be used as oxidants. Of course, oxygen gas mixed at varying percentages in other gases, such as helium, neon, argon, nitrogen or even carbon dioxide.

It has also been determined that the volume of solvent in the reaction mixture can have an effect on the partial oxidation process. In particular, the molar ratio of solvent to allyl ether should be from about 47:1 to about 200:1, or from about 94:1 to about 190:1. Acetonitrile has been found to be a suitable solvent, but other solvents such as chloroform, dichloromethane, N,N-dimethylformamide, N,N-dimethylacetamide, dimethyl sulfoxide, or dimethylcarbonate can be used in the process.

Advantageously, the reaction solution can further include trichloromethyl cyanide or N-hydroxyphthalimide (NHPI) to promote partial oxidation.

When the direct partial oxidation process is conducted according to the present disclosure, the conversion of allyl ether to allyl acrylate can be from about 10% to about 92%, and the selectivity for allyl acrylate can be from about 40% to about 100%.

EXAMPLES

Preparation of Catalysts
Chemicals:
Manganese (II) nitrate tetrahydrate $(Mn(NO_3)_2 \cdot 4H_2O$, ≥97.0%), 1-butanol (anhydrous, 99.8%), and Pluronic P123, a poly(ethylene glycol)-block-polypropylene glycol)-block-poly(ethylene glycol) (PEO20-PPO70-PEO20), lithium nitrate, sodium nitrate, potassium nitrate, cesium nitrate, rubidium nitrate, calcium nitrate, barium nitrate and strontium nitrate were used for preparing different catalysts. For substrate scope: allyl ether, 2,5-dihydrofuran, allyl acrylate, allyl glycidyl ether, and allyl phenyl ether were used in presence of toluene as solvent. The substrates and $\alpha$-$Mn_2O_3$ were purchased from Sigma-Aldrich. Concentrated nitric acid ($HNO_3$, 68-70%) was purchased from J. T. Baker. All chemicals were used as received without further purification.

Synthesis of Metal Oxides:
In a typical synthesis 0.02 mol of manganese nitrate tetrahydrate $(Mn(NO_3)_2 \cdot 4H_2O)$ and 0.134 mol of 1-butanol were added into a 120 mL beaker. To this solution 0.00034 mol of Pluoronic P123 (molar mass 5750 g mol$^{-1}$) and 0.032 mol of concentrated nitric acid ($HNO_3$) were added and stirred at room temperature until the solution became clear (light pink). The resulting clear solution was then kept in an oven at 120° C. for 3 hours under air. A black product was collected and washed with excess ethanol, centrifuged, and dried in a vacuum oven overnight. At the end, the dried black powders were subjected to a heating cycle. First they were heated at 150° C. for 12 hours and cooled down to room temperature under ambient conditions followed by a second heating step of 250° C. for 3 hours. For other metal oxides, similar procedure was followed.

Small amount of metal promoters can significantly aid oxygen transport in heterogeneous partial oxidation of allyl ether. Typically these promoters can polarize and thereby activate the double bond of $O_2$, can create cation vacancies to aid hydrocarbon substrate binding and often decorate surface sites of redox active metal oxide to electronically make each site more active for oxidation. After calcination, metal oxides were placed in a crucible. Onto this 1M of group 1 or group 2 metal ion solutions were added drop-wise in calculated amounts up to 1 mol % of the metal oxide. After wetness impregnation was done, the crucibles were left for drying and finally they were calcined at 250° C. for 30 minutes.

Example 1

In order to compare the effectiveness of various catalysts for direct oxidation of allyl ether, 1 mmole of allyl ether was dissolved in 2.5 mL of acetonitrile and 1.1 equivalents of t-butyl hydroperoxide (TBHP) was added. A quantity of 25 mg of each catalyst was added to separate solutions as described above, and the mixtures were heated to 80° C. for 5 hours.

Table 1 below provides a comparison of the effectiveness of the various catalysts for the partial oxidation of allyl ether to form allyl acrylate.

TABLE 1

| Run # | Catalyst (25 mg) | Conversion (%) | Selectivity for Allyl Acrylate (%) |
|---|---|---|---|
| 1 | Meso-MnOx | 41 | 100 |
| 2 | Meso-CoOx | <1 | 100 |
| 3 | Meso-SiOx | <1 | 100 |
| 4 | Amorphous Mn Oxide | <1 | 100 |
| 5 | $\alpha$-$Mn_2O_3$ | 20 | 100 |
| 6 | Meso-$Al_2O_3$ | <1 | 100 |

It is clear that under the specified conditions the mesoporous manganese oxide was the most effective catalyst of those studied.

Example 2

The MnOx catalyst was impregnated with various Group I and Group II promoter ions, as described above. One mmole of allyl ether was dissolved in 2.5 mL of acetonitrile and 1.1 equivalents of TBHP was added. A quantity of 25 mg of each promoted catalyst was added to separate solutions as described above, and the mixtures were heated to 80° C. for 5 hours.

Table 2 below compares the effectiveness of the various ion promoted MnOx catalysts for partial oxidation of allyl ether to form allyl acrylate.

TABLE 2

| Run # | Catalyst (25 mg) | Conversion (%) | Selectivity for Allyl Acrylate (%) |
|---|---|---|---|
| 1 | Li—MnOx | 90 | 100 |
| 2 | Na—MnOx | 90 | 67 |
| 3 | K—MnOx | 88 | 56 |
| 4 | Rb—MnOx | 97 | 92 |
| 5 | Cs—MnOx | 88 | 100 |
| 6 | Ca—MnOx | 86 | 100 |
| 7 | Sr—MnOx | 89 | 100 |
| 8 | Ba—MnOx | 74 | 100 |

In run numbers 2-4, significant amounts of epoxides were detected as byproducts. However, this testing demonstrated that Group I and Group II ions are effective promoters for MnOx catalysts, greatly increasing the conversion percentage as compared to Example 1, run 1, which used MnOx alone as the catalyst.

Example 3

Additional testing was conducted to evaluate the effectiveness of various oxidants for use in the direct partial oxidation of allyl ether to form allyl acrylate. Except as otherwise specified, 1 mmole of allyl ether was dissolved in 2.5 mL of acetonitrile, 2 equivalents of trichloromethyl cyanide and 25 mg of the indicated oxidant were added. A quantity of 25 mg of Li-MnOx catalyst was added to separate solutions as described above, and the mixtures were heated to 80° C. for 5 hours.

Table 3 below compares the effectiveness of the various oxidants for partial oxidation of allyl ether to form allyl acrylate.

TABLE 3

| Run # | Oxidant | Conversion (%) | Selectivity for Allyl Acrylate (%) |
|---|---|---|---|
| 1 | TBHP | 90 | 100 |
| 2 | $H_2O_2$ | 10 | 40 |
| 3 | m-CPBA[a] | 30 | 100 |
| 4 | NHPI-air | 92 | 100 |
| 5[b] | NHPI-air | 60 | 100 |
| 6[c] | NHPI-air | 85 | 100 |
| 7 | cumene hydroperoxide | 55 | 100 |
| 8 | benzoyl peroxide | 90 | 100 |
| 9 | peracetic acid | 90 | 63 |

[a]m-chloroperoxybenzoic acid;
[b]2 hours;
[c]in absence of $Cl_3CCN$

The testing in Example 3 demonstrated that a number of different oxidants, including air, can be used in the direct partial oxidation of allyl ether to form allyl acrylate. Runs 4-6 demonstrate that using air as an oxidant results in high conversion as well as high selectivity for allyl acrylate. In run 2 significant amounts of epoxide were detected as byproducts.

Example 4

In order to observe the effect of solvent volume in the partial oxidation reactions, 1 mmole of allyl ether was dissolved in varying quantities of acetonitrile and 1.1 equivalent of TBHP oxidant was added. A quantity of 25 mg of Li-MnOx catalyst was added to separate solutions, and the mixtures were heated to 80° C. for 5 hours.

Table 4 below compares the effect of the varying the quantity of solvent in partial oxidation of allyl ether to form allyl acrylate.

TABLE 4

| Run # | Solvent volume (mL) | Conversion (%) | Selectivity for Allyl Acrylate (%) |
|---|---|---|---|
| 1 | 1 | 8 | 100 |
| 2 | 2.5 | 90 | 100 |
| 3 | 5 | 92 | 100 |
| 4 | 10 | 90 | 100 |

The data in Table 4 demonstrate that solvent volume plays a key role in mediating oxygen transport during the reaction.

Example 5

In order to explore the scope of direct partial oxidation reactions, some other allyl ether derivatives were subjected to the process. In these tests, 1 mmole of each substrate was dissolved in 2.5 mL of toluene, 25 mg of Li-MnOx was added, and 1.2 equivalents of NHPI was added. The mixtures were heated to 80° C. for 5 hours.

TABLE 5

| Run # | Substrate | Conversion (%) |
|---|---|---|
| 1 | allyl ether | 92 |
| 2 | allyl acetate | 60 |
| 3 | dihydrofuran | 100 |

TABLE 5-continued

| Run # | Substrate | Conversion (%) |
|---|---|---|
| 4 | allyl glycidyl ether | 66 |
| 5 | allyl phenyl ether | 12 |

The data in Table 5 demonstrate that various analogs of allyl ether can be partially oxidized directly.

PCT/EP Clauses:

1. A process for forming allyl acrylate, comprising contacting allyl ether in solution with a solvent with one or more oxidants in the presence of a mesoporous manganese oxide (MnOx) catalyst.

2. The process according to clause 1, wherein the oxidant is an oxygen-containing gas, such as air.

3. The process according to clause 1, wherein the oxidant is a peroxide.

4. The process according to any one of clauses 1 to 3, wherein the oxidant is a mixture of air and a peroxide.

5. The process according to any one of clauses 1 to 4, wherein the solvent is selected from acetonitrile, chloroform, dichloromethane, N,N-dimethylformamide, N,N-dimethyl acetamide, dimethyl sulfoxide, or dimethylcarbonate.

6. The process according to any one of clauses 1 to 5, wherein the solution further comprises trichloromethyl cyanide and/or N-hydroxyphthalimide (NHPI).

7. The process according to any one of clauses 1 to 6, wherein the mesoporous manganese oxide catalyst is promoted with promoter cations of Group I or Group II metals.

8. The process according to any one of clauses 1 to 7, wherein wherein the promoter ions are selected from the group consisting of Li, Na, K, Rb, Cs, Ca, Sr and Ba ions and combinations thereof, and are advantageously Li ions.

9. The process according to any one of clauses 1 to 8, wherein the mole ratio of solvent to allyl ether is from 47:1 to 200:1.

10. The process according to any one of clauses 1 to 9, wherein from 94:1 to 190:1.

11. The process according to any one of clauses 1 to 10, wherein the conversion of allyl ether to allyl acrylate is from 10% to 92%, and the selectivity for allyl acrylate is from 40% to 100%.

12. The process according to any one of clauses 1 to 11, wherein the process is conducted at temperatures from from 10° C. to 110° C., or from 40° C. to 90° C., or even from 45° C. to 80° C.

13. The process according to any one of clauses 1 to 12, wherein the process is conducted at pressures from 0.1 atm to 3 atm.

14. The process according to any one of clauses 1 to 13, wherein the process is conducted over a period of from 0.1 hour to 16 hours, or from 1 hour to 10 hours, or even from 2 hours to 5 hours.

INDUSTRIAL APPLICABILITY

The systems and methods disclosed herein are applicable to the chemical industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A process for forming allyl acrylate, comprising contacting allyl ether with a solvent, wherein the solvent is selected from acetonitrile, chloroform, dichloromethane, N,N-dimethylformamide, N,N-dimethyl acetamide, dimethyl sulfoxide, or dimethylcarbonate, and with an oxidant, wherein the oxidant is selected from oxygen, oxygen-containing gases, peroxides, and mixtures thereof in the presence of a mesoporous manganese oxide (MnOx) catalyst.

2. The process of claim 1, wherein the solution further comprises trichloromethyl cyanide and/or N-hydroxyphthalimide.

3. The process of claim 1, wherein the mesoporous manganese oxide catalyst is promoted with promoter cations of Group I or Group II metals.

4. The process of claim 3, wherein the promoter ions are selected from the group consisting of Li, Na, K, Rb, Cs, Ca, Sr and Ba ions, and combinations thereof.

5. The process of claim 4, wherein the promoter ions are Li ions.

6. The process of claim 1, wherein the mole ratio of solvent to allyl ether is from 47:1 to 200:1.

7. The process of claim 6, wherein the mole ratio of solvent to allyl ether is from 94:1 to 190:1.

8. The process of claim 1, wherein the conversion of allyl ether to allyl acrylate is from 10% to 92%.

9. The process of claim 1, wherein the selectivity for allyl acrylate is from 40% to 100%.

10. The process of claim 1, which is conducted at a temperature of from 10° C. to 110° C.

11. The process of claim 1, which is conducted at a temperature of from 40° C. to 90° C.

12. The process of claim 1, which is conducted at a temperature of from 45° C. to 80° C.

13. The process of claim 1, which is conducted at a pressure of from 0.1 atm to 3 atm.

14. The process of claim 1, which is conducted over a period from 0.1 hour to 16 hours.

15. The process of claim 1, which is conducted over a period from 1 hour to 10 hours.

* * * * *